United States Patent
Kochat

(10) Patent No.: US 6,504,049 B1
(45) Date of Patent: Jan. 7, 2003

(54) PROCESS FOR SYNTHESIZING PHARMACEUTICALLY ACTIVE DISULFIDE SALTS

(75) Inventor: Harry Kochat, San Antonio, TX (US)

(73) Assignee: BioNumerik Pharmaceuticals, Inc., San Antonio, TX (US)

( * ) Notice: Subject to any disclaimer, the term of this patent is extended or adjusted under 35 U.S.C. 154(b) by 0 days.

(21) Appl. No.: 10/135,756

(22) Filed: Apr. 30, 2002

(51) Int. Cl.$^7$ .......................... C07C 309/05; C07F 9/30
(52) U.S. Cl. ........................ 562/103; 562/20; 562/23
(58) Field of Search ........................... 562/20, 23, 103

(56) References Cited

FOREIGN PATENT DOCUMENTS

WO            9814426       *    4/1998

* cited by examiner

Primary Examiner—Joseph K. McKane
Assistant Examiner—Sonya Wright
(74) Attorney, Agent, or Firm—Thomas J. Dodd

(57) ABSTRACT

A process for synthesizing pharmaceutically active disulfides, particularly Dimesna and certain derivatives thereof. The process includes reacting an alkylene salt with a sulfurating reagent, then alkalizing the intermediate and flowing oxygen through the mixture to produce the final compound in high yield.

7 Claims, No Drawings

PROCESS FOR SYNTHESIZING PHARMACEUTICALLY ACTIVE DISULFIDE SALTS

FIELD OF THE INVENTION

This invention relates to a process for synthesizing disulfide salts, and will have application to a process for synthesizing pharmaceutically active disulfides.

BACKGROUND OF THE INVENTION

Disodium 2,2'-dithiobis ethane sulfonate (Dimesna), and other salts and derivatives thereof, are known chemotherapeutic protective agents used to mitigate the toxicity of platinum complex antitumor drugs which are given to patients with certain types of cancer. Disclosure of Dimesna and like compounds as platinum protecting agents are found in U.S. Pat. Nos. 5,789,000; 5,866,169; 5,866,615; 5,866,617; and elsewhere in the literature.

Dimesna is a physiological auto-oxidation product of sodium 2-mercaptoethane sulfonate (Mesna), which is also a protective agent for chemotherapeutic drugs. The structures of the preferred sodium salts (disodium in the case of the dianionic Dimesna molecule) of Mesna and Dimesna are seen below as formula I and formula II, respectively.

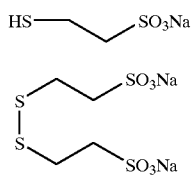

Both Mesna and Dimesna have been used with varying degrees of success as protective agents for administration with platinum complex anti-tumor drugs. In particular, Dimesna has been shown to be effective in providing protection against cisplatin (cis-diammine dichloro platinum) induced nephrotoxicity, and both Mesna and Dimesna have been shown to be effective against carboplatin (cis-diammine-1,1 cyclobutane dicarboxylato platinum) induced myelosuppression. Mesna has also been used as a protective agent with other antitumor drugs, and is approved for such use in the United States and a number of foreign jurisdictions. Full disclosures on the action of Mesna, Dimesna, and derivatives of each is found in one or more of the above referred documents, and more may also be found in the published literature. The wide-ranging utility of both Mesna and Dimesna as protective agents has been established in this art.

As mentioned above, Mesna is auto-oxidized in the body to Dimesna under mildly basic conditions and in the presence of oxygen, such as those present in plasma. Prior synthetic methods of making Dimesna involved the oxidation of Mesna to form its dimer (Dimesna) in substantially quantitative yield. This synthesis was accomplished by reacting the dissolved Mesna with an oxidizing agent, which contained a source of elemental iodine as the oxidant, or in iodate form in an aqueous medium.

The prior art processes for synthesizing Mesna and Dimesna (and like sulfhydryls and disulfides) include the conversion of various alkyl sulfonic acids into their respective mercaptane derivatives and the subsequent oxidation into their respective disulfides by use of iodine-containing reagents as an oxidizing reagent. These processes, while efficient, required isolation procedures to be performed to isolate and purify the end products from the reagents used. Further, environmental pollutants were generated by the prior art processes which required disposal. Finally, the prior art processes could not be carried out in a single-pot process.

Applicant has previously devised a two step, single pot process for synthesizing Dimesna through the oxidation of Mesna. This process is disclosed in U.S. Pat. No. 5,808,140; and in U.S. patent application Ser. No. 09/108,168, filed Jun. 30, 1998, allowed.

SUMMARY OF THE INVENTION

The process of this invention includes a two step, single pot method of synthesizing Dimesna and derivatives thereof from commonly available starting materials.

The first step of the process involves the synthesis of a key intermediate, an S-acetyl derivative of the desired disulfide. Addition of a strong base and a source of oxygen converts the key intermediate to the desired disulfide.

The compounds synthesized by the process are useful as pharmaceuticals, particularly those uses referred to above, as well as other pharmaceutical uses.

Accordingly, it is an object of this invention to provide for a novel process of synthesizing pharmaceutically active disulfides.

Another object of this invention is to provide for a process of synthesizing disulfides which is efficient and economical.

Other objects of this invention will become apparent upon a reading of the following description.

DESCRIPTION OF THE PREFERRED EMBODIMENTS

The preferred embodiments herein described are not intended to be exhaustive or to limit the invention to the precise form disclosed. They are chosen and described to explain the principles of the invention and its application and practical use to enable others skilled in the art to understand its teachings.

The process of this invention comprises two steps and functions to synthesize the desired disulfide end product from commercially available starting materials. The disulfides to be synthesized have the following formula I:

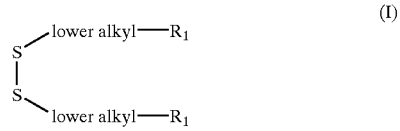

wherein $R_1$ is sulfonate or phosphonate and lower alkyl denotes a straight or branched chain hydrocarbon with one to six total carbon atoms.

The following schemes illustrate the general process employed by this invention.

Scheme 1

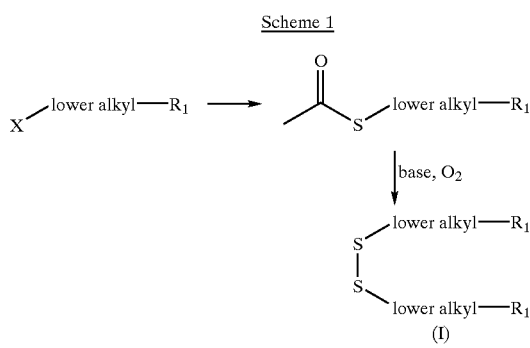

Scheme 1 illustrates a synthesis of the formula I compounds according to this invention. In the diagram, X is a leaving group, preferably a halogen atom, and lower alkyl and $R_1$ are as defined above.

All processes may be carried out in aqueous solution. The starting material is converted to the key intermediate, an S-acetyl derivative of the starting material, through a substitution reaction wherein the leaving group is replaced by the S-acetyl moiety shown. A preferred reactant to facilitate this conversion is an alkali metal salt of thioacetic acid.

Step two of the process is preferably carried out in the same reactant vessel (pot), and involves the addition of a strong base and a source of oxygen gas to convert the thioacetate intermediate to its sulfhydryl form and thence to its oxidized disultide. As a result of the processes used, the formula I compounds will preferably be symmetrical disulfides.

Scheme 2

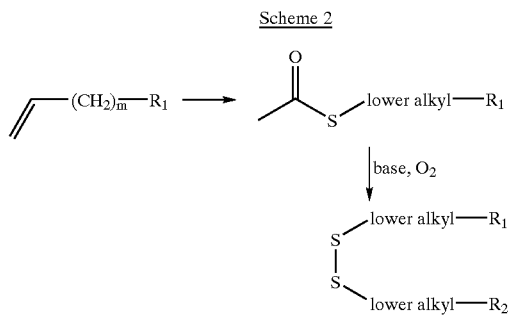

Scheme 2 illustrates an alternative starting material for the process of this invention. As depicted, the process is the same as in Scheme I, but the starting material is an alkenyl alkylene salt, which is converted to the key thioacetate intermediate by addition of an alkali metal salt of thioacetic acid. As in Scheme 1, the resulting thioacetate intermediate is converted to a formula I disulfide by addition of a strong base and a source of oxygen.

The following specific examples are illustrative of the process of this invention.

EXAMPLE 1

Preparation of Diethyl S-Acetyl-Methylmercapto Phosphonate

To a solution of disodium bromomethyl phosphonate (2.6 g) in anhydrous tetrahydrofuran is added solid potassium thioacetate (5.2 g) and stirred at room temperature for 15 hours. The organic portion is then taken up in ether (200 mL) and washed with water (100 mL×3). The organic portion is then dried over anhydrous sodium sulfate, filtered and concentrated to dryness. The product is then analyzed by NMR.

$^1$H-NMR: □ 2.23 (3H, s), 2.72 (2H, m), 3.01 (2H, m)

EXAMPLE 2

Preparation of Sodium S-Acetyl-2-Mercaptoethane Sulfonate

2-Bromoethane sulfonic acid, monosodium salt (25 gram) in 250 mL process water and added potassium thioacetate (20.6 gram). The reaction mixture is then heated to reflux for 12 hours. The reaction mixture is then concentrated to 100 mL volume at 80° C. under reduced pressure and the product is crystallized out directly. The product is then characterized by NMR.

$^1$H-NMR: □ 2.22 (3H, s), 2.7 (2H, m), 3.01 (2H, m)

EXAMPLE 3

Preparation of Disodium 2,2'-Dithiobis-ethane Sulfonate

The ongoing S-acetyl-2-mercaptoethane sulfonic acid, sodium salt (20 g) is dissolved in water and added 1N sodium hydroxide to adjust the pH to 9.0. The reaction mixture is the then stirred while bubbling oxygen for 48 hours. The aqueous portion is then concentrated and crystallized out the product directly. Yield is found to be 80%. The product is characterized by NMR and corroborated the structure with the authentic sample.

$^1$H-NMR: □ 2.8–2.9 (2H, m); 3.1–3.2 (2H, m)

EXAMPLE 4

Preparation of Sodium S-Acetyl-2-Mercaptoethane Sulfonate

Vinyl sulfonic acid, monosodium salt (25% aqueous solution, 100 mL) is taken in a flask equipped with reflux condenser and to it is added potassium thioacetate (20.6 g). The reaction mixture is then heated to reflux for 96 hours. The reaction mixture is then concentrated to 50 mL volume at 80° C. under reduced pressure and the product is crystallized out directly. The product is then characterized by NMR.

$^1$H-NMR: □ 2.22 (3H, s), 2.7 (2H, m), 3.01 (2H, m)

What is claimed is:

1. A process for synthesizing a compound of the formula:

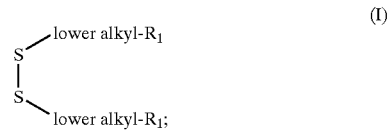

wherein $R_1$ is sulfonate or phosphonate, said process comprising the steps of:

(i) providing a starting material of the formula:

wherein X is a leaving group; and dissolving the starting material in a reactant vessel;

(ii) reacting the starting material with a sulfurating reagent to produce the intermediate:

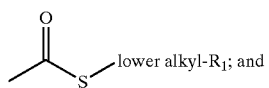 (III)

(iii) reacting the intermediate with a base and a source of oxygen to produce the formula I compound.

2. The process of claim 1 wherein X is a halogen, and the sulfurating reagent is an alkali metal salt of thioacetic acid.

3. The process of claim 1 wherein X is $CH_2=CH-$.

4. The process of claim 1 wherein said base is a strong base.

5. The process of claim 4 wherein said strong base is sodium hydroxide.

6. The process of claim 1 wherein said source of oxygen is oxygen gas, which is bubbled into the reactant vessel.

7. The process of claim 1 wherein the process is carried out in aqueous solution.

* * * * *